United States Patent [19]

Masi et al.

[11] 4,134,903

[45] Jan. 16, 1979

[54] ANTHRACYCLINE ETHERS AND THEIR PREPARATION

[75] Inventors: Paolo Masi; Antonino Suarato; Pietro Giardino; Luigi Bernardi, all of Milan; Federico Arcamone, Nerviano (Milan), all of Italy

[73] Assignee: Societa Farmaceutici Italia S.p.A., Milan, Italy

[21] Appl. No.: 887,782

[22] Filed: Mar. 17, 1978

Related U.S. Application Data

[62] Division of Ser. No. 817,972, Jul. 22, 1977, Pat. No. 4,088,569.

[30] Foreign Application Priority Data

Aug. 7, 1976 [GB] United Kingdom ............... 32992/76

[51] Int. Cl.² ...................... C07C 49/72; C07C 49/73; C07C 97/26; C09B 1/30
[52] U.S. Cl. ................................................ 260/365
[58] Field of Search ................................ 260/365, 376

[56] References Cited

U.S. PATENT DOCUMENTS

| | | | |
|---|---|---|---|
| 3,665,018 | 5/1972 | Jolles | 260/365 |
| 3,686,163 | 8/1972 | Arcamone et al. | 260/365 |
| 4,077,988 | 3/1978 | Arcamone et al. | 260/376 |

OTHER PUBLICATIONS

*Canadian Jol. of Chemsitry*, vol. 49, No. 16, Sep., 1971, Wong et al., "Synthetic Studies of Hydronapthacenic Antibiotics, I. The Synthesis of 4-Demethoxy-7-O-methyl Daunomycinone", pp. 2712–2718.

*Primary Examiner*—Allen B. Curtis
*Assistant Examiner*—Raymond Covington

*Attorney, Agent, or Firm*—Hubbell, Cohen, Stiefel & Gross

[57] ABSTRACT

Aglycones of the formula

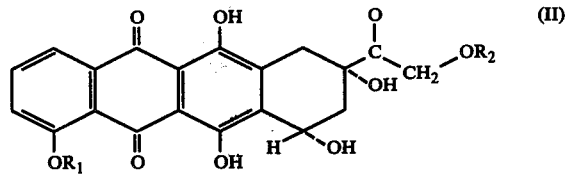

and Toslyhydrazones of the formula

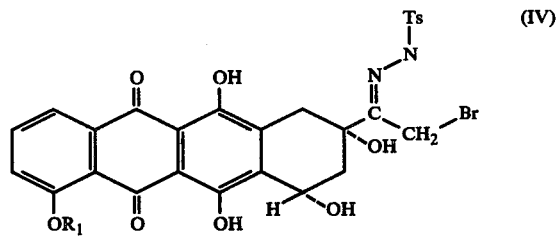

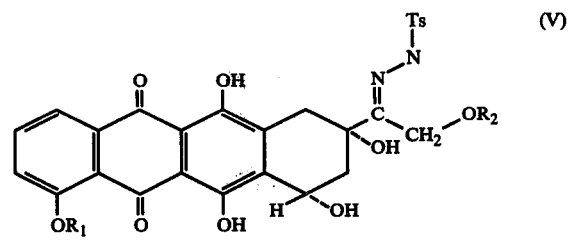

wherein $R_1$, $R_2$ and Ts have meanings described in the specification, and process for preparing a compound of formula (V).

12 Claims, No Drawings

ANTHRACYCLINE ETHERS AND THEIR PREPARATION

The invention described herein was made in the course of work under a grant from the U.S. Department of Health, Education and Welfare.

CROSS REFERENCE TO RELATED APPLICATIONS

This is a division of application Ser. No. 817,972, filed July 22, 1977 now U.S. Pat. No. 4,088,569.

BACKGROUND OF THE INVENTION

1. Field of the Invention

The present invention relates to daunomycin analogues (i.e., 14-alkoxy (or aryloxy) daunomycins), a method for making them, certain novel intermediates which are used in the method for making them, methods for making the intermediates and methods of using the daunomycin analogues in treating certain amamalian tumors.

2. The Prior Art

Daunomycin as well as its aglycone - daunomycinone are, of course, known compounds. Moreover, 14-bromodaunomycinone is also a known compound.

The compounds according to the invention, as will appear below, are α-alkoxy (or aryloxy) ketones inasmuch as they possess the

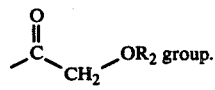

It has long been known from the literature (S. Patai. The Chemistry of Ether Linkage, 480 (1976; Interscence Publishers)) that α-alkoxyketones can be prepared from the relatively inaccessible diazoketones by a rather complicated overall process. Possible alternative methods for producing such compounds, such as by the nucleophilic substitution of a halogen atom in an α-haloketone by an alkoxyl anion, however, yield different products, namely epoxyethers, α-hydroxyketals and α-hydroxyketones (J. Am. Chem. Soc. 74, 618 (1952) and ibid 78 (1956)), or compounds resulting from Favorsky rearrangement (Organic Reactions 11, 261 (1960)).

Moreover, it has been ascertained that 14-bromodaunomycinone does not react directly with alcohols in the presence of silver salts or silver oxide.

SUMMARY OF THE INVENTION

The present invention in addition to providing novel daunomycin analogues, also provides a method for making them which avoids the disadvantages noted above in connection with the prior art.

In one aspect, the invention provides novel daunomycin analogues (daunomycin ethers) of the formula:

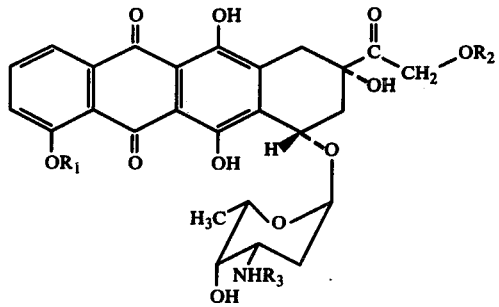

wherein $R_1$ is hydrogen or a $C_1$–$C_4$ lower alkyl, $R_2$ is a $C_1$–$C_4$ lower alkyl, a $C_3$–$C_6$ cycloalkyl, phenyl, lower alkyl phenyl, lower alkoxy phenyl or halophenyl, and $R_3$ is hydrogen or a trifluoroacetyl group.

The synthesis of these daunomycin analogues I utilizes an original process for the preparation of the new aglycones of the formula II, which are analogues of daunomycinone, wherein $R_1$ and $R_2$ are as defined above:

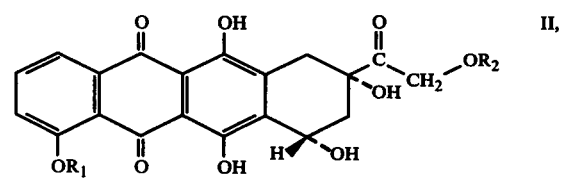

which aglycones II are subsequently condensed with a sugar moiety to produce the compounds of formula I. The aglycones of formula II are also a part of the present invention. As noted above, the known compound, 14-bromodaunomycinone, which is a convenient starting material for the ultimate preparation of compounds of formula I can not be directly converted into 14-alkoxy (or aryloxy) derivatives and thus, cannot be directly converted to the aglycones II.

It has now surprisingly been found that if 14-bromodaunomycinone (III; $R_1$=$CH_3$)

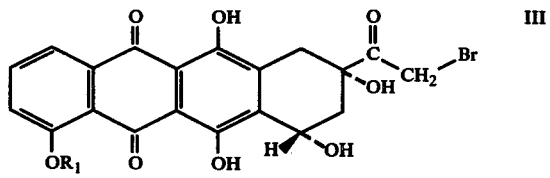

is converted to the tosylhydrazone IV, the latter can then be easily transformed into the corresponding 14-alkoxy or 14-aryloxy derivative V, wherein $R_1$ and $R_2$ are as defined above:

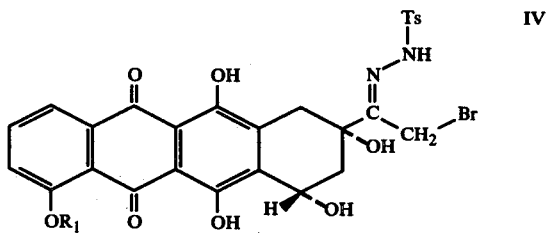

-continued

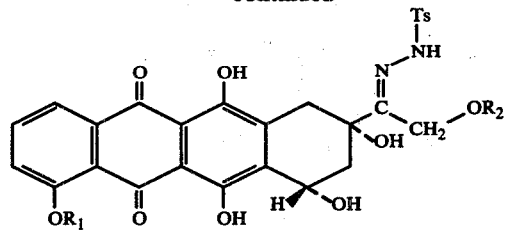

Ts = tosyl group

The intermediates of formulae IV and V are, of course, also novel compounds which also form part of the invention.

The above reaction is carried out at a temperature between 0° and 50° C., but usually at room temperature, by dissolving a compound of formula IV (a tosylhydrazone) in an alcohol of the formula $R_2OH$, wherein $R_2$ is as defined above and adding to the solution either a silver salt or oxide, or a base such as sodium or potassium carbonate, hydroxide and the like. The replacement of the bromine atom in the 14-position by the alkoxy (or aryloxy) group is very fast and clean, and yields a compound of formula V in very high yield.

The intermediate compound of formula V is then refluxed in acetone in the presence of a trace amount of p-toluensulphonic acid to form the aglycone II in almost quantitative yield.

The new antitumor compounds of formula I are then obtained from the above aglycones II according to the process described in Belgian Patent No. 830,090 (owned by the unrecorded assignee hereof). Thus, according to that process, an aglycone of the formula II is condensed with 2,3,6-trideoxy-3-trifluoroacetamido-4-O-trifluoroacetyl-α-L-lyxopyranosyl chloride in the presence of a silver salt or silver oxide to form the intermediate VI, which, on treatment with methanol, is converted to the desired compound I ($R_3$=$CF_3CO$):

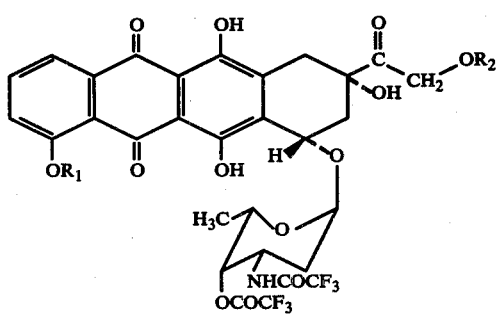

Subsequent treatment of compound I ($R_3$=$CF_3CO$) with NaOH affords the corresponding glycoside I ($R_3$=H). The new compounds I $R_3$=H or $CF_3CO$ display antimitotic activity and are useful therapeutic agents for the treatment of tumor diseases in mammals.

DESCRIPTION OF THE PREFERRED EMBODIMENTS

The preparation of compounds according to the invention will now be described in detail. All parts given are by weight unless otherwise indicated.

EXAMPLE 1

14-Bromodaunomycinone tosylhydrazone

Twenty-four grams of 14-bromodaunomycinone were suspended in 2 liters of a 1:1 mixture of methylene chloride-acetonitrile containing 2 ml. of acetic acid. Twelve grams of tosylhydrazine were added and the resulting suspension was refluxed for 10 hours. After cooling, 21 g. of 14-bromodaunomycinone tosylhydrazone were collected by filtration and washed with methylene chloride.

IR (KBr pellet): no ketone band, 1165 $cm^{-1}$ ($SO_2$).

EXAMPLE 2

14-Ethoxydaunomycinone tosylhydrazone

Four grams of 14-bromodaunomycinone tosylhydrazone were suspended in 150 ml. of ethanol and treated with 15 ml. of a saturated aqueous solution of $Na_2CO_3$ under stirring for 2 hours. After acidification with oxalic acid, the solvent was evaporated off in vacuo and the residue taken up in chloroform and washed several times with distilled water. The solvent was again removed in vacuo and the residue was chromatographed on silica gel to give pure 14-ethoxydaunomycinone tosylhydrazone. PMR (DMSO-d6): 1.20 (t, 3H ($CH_2$)$CH_3$), 2.41 (s, 3H, $CH_3$—Ph—$SO_2$), 3.36 (q, 2H, $OCH_2(CH_3)$), 3.86 (s, 3H, —$OCH_3$),

4.96 (broad s, C-7-H), 7.03–8.10 δ(m, 7H, aromatic protons). The product, on twin layer chromatography (TLC), using the solvent system: chloroform-acetone (8:2, v/v) had an Rf = 0.56.

EXAMPLE 3

14-Ethoxydaunomycinone tosylhydrazone

To 7.5 grams of 14-bromodaunomycinone tosylhydrazone dissolved in 800 ml. of a 1:1 mixture of methylene chloride-ethanol, a solution of 3.08 g. of silver trifluoromethansulphonate in diethyl ether was added. After stirring for 1 hour at room temperature, the solution was neutralized with aqueous $NaHCO_3$ and the solvent evaporated in vacuo. The residue was taken up in chloroform and washed with distilled water. The chloroform was evaporated off in vacuo and the residue taken up in diethyl ether and collected by filtration to give 6.35 g. of a compound identical with the product reported in Example 2.

EXAMPLE 4

14-Methoxydaunomycinone tosylhydrazone

Starting from 7.5 g. of 14-bromodaunomycinone tosylhydrazone and operating as described in Example 3, but using methanol instead of ethanol, there were obtained 6.5 g. of 14-methoxydaunomycinone tosylhydrazone. PMR (DMSO$_{d6}$): 2.26 (s, 3H, $CH_3$—(P-h)—$SO_2$), 3.20 (s, 3H, ($CH_2$)—$OCH_3$), 3.83 (s, 3H (C-4-$OCH_3$),

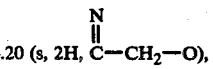

4.83 (broad s, 1H, C-7-H), 6.96–7.96 δ(m, 7H, aromatic protons).

EXAMPLE 5

14-Isopropyloxydaunomycinone tosylhydrazone

From 7.5 g. of 14-bromodaunomycinone tosylhydrazone, but using isopropanol instead of ethanol, there were obtained 3.6 g. of 14-isopropyloxydaunomycinone tosylhydrazone following the reaction conditions reported in Example 3. PMR (CDCl$_3$): 1.21 (d, (CH$_3$)$_2$C(H)), 2.42 (s, CH$_3$-C$_6$(H$_4$)), 3.96 (s, CH$_3$O), 4.50 (s, =C—CH$_2$—O), 5.10 (broad s, C-7-H), 7.0–8.0 (m, 7 aromatic protons), 9.90 (s, NH) and 12.90 and 13.50 δ (two s, phenolic hydroxyls).

EXAMPLE 6

14-Phenoxydaunomycinone tosylhydrazone

Following the procedure described in Example 3, but using phenol instead of ethanol, there were obtained 5.7 g. of 14-phenoxydaunomycinone tosylhydrazone starting from 7.5 g. of 14-bromodaunomycinone tosylhydrazone. PMR (CDCl$_3$): 2.40 (s, CH$_3$—C$_6$(H$_4$)), 5.05 (broad s, C-7-H), 5.15 (s, =C—CH$_2$—O), 6.8–8.1 δ (m, 12H, aromatic protons).

EXAMPLE 7

14-Ethoxydaunomycinone

A solution of 6.35 g. of 14-ethoxydaunomycinone tosylhydrazone in 400 ml. of acetone containing a catalytic amount of p-toluensulphonic acid monohydrate was refluxed for 4 hours. After cooling and neutralization with aqueous NaHCO$_3$, the solvent was removed in vacuo and the residue taken up in chloroform, washed with water and purified by column chromatography to yield 3.5 g. of 14-ethoxydaunomycinone. PMR (CDCl$_3$ + DMSO$_{d6}$): 1.25 (t, 3H, O(CH$_2$)CH$_3$), 3.53 (q, 2H, OCH$_2$(CH$_3$)), 3.95 (s, 3H, OCH$_3$), 4.66 (s, 2H, COCH$_2$O), 5.08 (broad s, C-7-H), 7.13–8.00 δ (m, 3H, aromatic protons). TLC: solvent system chloroform-acetone (8:2), v/v); Rf = 0.50.

EXAMPLE 8

14-Methoxydaunomycinone

Following the procedure described in Example 7, 2.6 g. of 14-methoxydaunomycinone were prepared from 5 g. of 14-methoxydaunomycinone tosylhydrazone. PMR (CDCl$_3$ + DMSO$_{d6}$): 3.40 (s, 3H, (CH$_2$)OCH$_3$), 3.96 (s, 3H, (C-4-OCH$_3$), 4.63 (s, 2H, COCH$_2$O), 5.13 (broad s, C-7-H), 7.13–7.90 δ (m, 3H, aromatic protons). TLC: solvent system chloroform-acetone (8:2, v/v); Rf = 0.37.

EXAMPLE 9

14-Isopropyloxydaunomycinone

Starting from 6 g. of 14-isopropyloxydaunomycinone tosylhydrazone and operating as described in Example 7, 4 g. of 14-isopropyloxydaunomycinone were obtained. PMR (CDCl$_3$ — DMSO$_{d6}$): 1.16 (d, 6H, CH(CH$_3$)$_2$), 3.56 (m, 1H, OCH(CH$_3$)$_2$), 3.93 (s, 3H, OCH$_3$), 4.63 (s, 2H, COCH$_2$O), 5.03 (broad s, C-7-H), 7.06–7.86 δ (m, 3H, aromatic protons). TLC: solvent system chloroform-acetone (8:2, v/v); Rf = 0.56.

EXAMPLE 10

14-Phenoxydaunomycinone

Following the procedure described in Example 7, 3.2 g. of 14-phenoxydaunomycinone were obtained from 6 g. of 14-phenoxydaunomycinone tosylhydrazone. PMR (CDCl$_3$): 4.08 (s, 3H, OCH$_3$), 4.86 (broad s, C-7-H), 5.33 (s, 2H, COCH$_2$O) 6.83–8.08 δ (m, 8H, aromatic protons). TLC: solvent system chloroform-acetone (8:2, v/v); Rf = 0.37.

EXAMPLE 11

Starting from 14-bromodaunomycinone tosylhydrazone and applying the procedures described in Examples 6 and 10, the following 14-aryloxydaunomycinones were prepared (the number given in brackets alongside each compound is the Rf on silica gel plates using the solvent system: chloroform-acetone 8:2 v/v):
14-p-chlorophenoxydaunomycinone — (0.41)
14-p-methoxyphenoxydaunomycinone — (0.39)
14-o-methylphenoxydaunomycinone — (0.37)
14-m-methoxyphenoxydaunomycinone — (0.38).

EXAMPLE 12

N-Trifluoroacetyl-14-ethoxydaunomycin

To a solution of 1.5 g. of 14-ethoxydaunomycinone and 1.25 g. of 2,3,6-trideoxy-3-trifluoroacetamido-4-0-trifluoroacetyl-α-L-lyxopyranosyl chloride in 100 ml. of anhydrous methylene chloride, a solution of 0.95 g. of silver trifluoromethane-sulphonate in anhydrous diethyl ether was added dropwise at room temperature under stirring. After 1 hour the reaction mixture was washed with aqueous NaHCO$_3$ and evaporated to dryness. The residue was dissolved in methanol containing 1 drop of triethylamine and let stand at room temperature for 2 hours. The solvent was removed in vacuo and the residue chromatographed (silica gel; chloroform-acetone 95/5) to give 0.9 g. of N-trifluoroacetyl-14-ethoxydaunomycin. PMR (CDCl$_3$): 1.33 (m, CH$_3$C(H$_2$) and CH$_3$C(H)), 5.60 (broad s, C-7-H), 5.40 (broad s, C-1'-H), 6.7–8.0 (m, 3 aromatic protons), and 12.90 and 13.70 δ (two phenolic protons).

EXAMPLE 13

N-Trifluoroacetyl-14-methoxydaunomycin

The condensation of 1.5 g. of 14-methoxydaunomycinone with 1.25 g. of 2,3,6-trideoxy-3-trifluoroacetamido-4-O-trifluoroacetyl-α-L-lyxopyranosyl chloride under the same reaction conditions described in Example 12 resulted in 0.75 g. of N-trifluoroacetyl-14-methoxydaunomycin. PMR (CDCl$_3$ + DMSO$_{6d}$): 1.33 (CH$_3$—C(H), 3.40 (s, 3H, C(H$_2$)OCH$_3$), 3.96 (s, CH$_3$O), 5.06 (broad s, C-7-H), 5.40 (broad s, C-1'-H), 6.7–8.0 (m, 3 aromatic protons) and 12.90 and 13.70 δ (two phenolic hydroxyls).

EXAMPLE 14

N-Trifluoroacetyl-14-isopropyloxydaunomycin

Following the procedure described in Example 12, and starting from 1.5 g. of 14-isopropyloxydaunomycinone and 1.25 g. of 2,3,6-trideoxy-3-trifluoroacetamido-4-0-trifluoroacetyl-α-lyxopyranosyl chloride, there was obtained 0.95 g. of N-trifluoroacetyl-14-isopropyloxydaunomycin. PMR (CDCl$_3$): 1.25 (d, CH$_3$—C(H) and (CH$_3$)$_2$C(H), 5.11 (broad s, C-7-H), 5.46 (broad s, C-1'-H) and 13.0 and 13.7 δ (two s, phenolic hydroxyls).

EXAMPLE 15

N-Trifluoroacetyl-14-phenoxydaunomycin

The reaction of 1.5 g. of 14-phenoxydaunomycinone with 1.2 g. of 2,3,6-trideoxy-3-trifluoroacetamido-4-O-trifluoroacetyl-α-L-lyxopyranosyl chloride under the conditions reported in Example 12 yielded 1.1 g. of N-trifluoroacetyl-14-phenoxydaunomycin. PMR ($CDCl_3$ + $DMSO_{d6}$): 1.32 (d, 3H, (C-5'-(H)-$CH_3$), 4.02 (s, 3H, $OCH_3$), 5.20 (broad s, C-7-H), 5.24 (s, 2H, $COCH_2$)), 5.50 (m, C-1'-H), 6.80–8.00 δ (m, 8H, aromatic protons). TLC: solvent system chloroform-acetone (8:2, v/v); Rf = 0.27.

EXAMPLE 16

Starting from the corresponding aglycones and applying the procedure described in Example 15, the following N-trifluoroacetyl analogues were prepared (the number given in brackets alongside each compound is the Rf on silica gel plates in the solvent system: chloroform acetone 8:2, v/v):

N-Trifluoroacetyl-14-p-chlorophenoxydaunomycin — (0.30)

N-Trifluoroacetyl-14-p-methoxyphenoxydaunomycin — (0.28)

N-Trifluoroacetyl-14-o-methylphenoxydaunomycin — (0.27)

N-Trifluoroacetyl-14-m-methoxyphenoxydaunomycin — (0.29).

EXAMPLE 17

14-Ethoxydaunomycin hydrochloride

Five hundred milligrams of N-trifluoroacetyl-14-ethoxydaunomycin were dissolved in 30 ml. of aqueous 0.15 NaOH and left standing for 1 hour at room temperature. After acidification with oxalic acid and rapid neutralization with aqueous $NaHCO_3$, the product was extracted with chloroform and the organic layer washed with water and evaporated to dryness. The residue was dissolved in methylene chloride and treated with 1 equivalent of HCl in methanol. By adding diethyl ether, 350 mg. of 14-ethoxydaunomycin hydrochloride precipitated and were collected by filtration. TLC: solvent system chloroform-methanol-water (13.6:1, v/v); Rf = 0.5.

EXAMPLE 18

14-Methoxydaunomycin hydrochloride

The hydrolysis of 1 g. of N-trifluoroacetyl-14-methoxydaunomycin, carried out under the same conditions as described in Example 17, yielded 0.750 g. of 14-methoxydanomycin hydrochloride. TLC: solvent system chloroform-methanol-water (13:6:1, v/v); Rf = 0.46.

EXAMPLE 19

14-Isopropyloxydaunomycin hydrochloride

The hydrolysis of 1 g. of N-trifluoroacetyl-14-isopropyloxydaunomycin was carried out as described in Example 17 to give 0.6 g. of 14-isopropyloxydaunomycin hydrochloride. TLC: solvent system chloroform-methanol-water (13:6:1, v/v) Rf = 0.59.

EXAMPLE 20

14-Phenoxydaunomycin hydrochloride

The hydrolysis of 1 g. of N-trifluoroacetyl-14-phenoxydaunomycin was carried out as described in Example 17 to give 0.6 g. of 14-phenoxydaunomycin hydrochloride. TLC: solvent system chloroform-methanol-water (13:6:1, v/v); Rf = 0.63.

EXAMPLE 21

Starting from the corresponding N-trifluoroacetyl analogues and applying to them the procedure reported in Example 20, the following 14-acyloxydaunomycins were prepared (the numbers given in brackets alongside each compound is the Rf on silica gel plates in the solvent system: chloroform/methanol/water 13/6/1).

14-p-chlorophenoxydaunomycin-HCl — (0.70)
14-p-methoxyphenoxydaunomycin-HCl — (0.68)
14-o-methylphenoxydaunomycin-HCl — (0.65)
14-m-methoxyphenoxydaunomycin-HCl — (0.68).

BIOLOGICAL ACTIVITY

The 14-alkoxy (an aryloxy) daunomycin analogues of the invention have been tested under the auspices of NCI — National Institute of Health — Bethesda, Md., U.S.A., against lymphocytic leukemia P 388 according to the procedure described in Cancer Chemotherapy Reports, Part 3, Vol. 3, page 9 (1972). The following tables illustrate the antitumor activity of some of the compounds of the invention.

TABLE 1

| Compound | Schedule of Treatment (ip) | Dose mole/Kg. | T/C % |
|---|---|---|---|
| 14-Ethoxydaunomycin-HCl | Days 1 to 9 | .0051 | 158 |
| | | .0025 | 144 |
| 14-Phenoxydaunomycin-HCl | Days 1 to 9 | .0190 | 179 |
| | | .0095 | 186 |
| | | .0047 | 179 |
| | | .0023 | 169 |
| Daunomycin-HCl | Days 1 to 9 | .0070 | 0 |
| | | .0035 | 137 |
| | | .0018 | 174 |
| | | .0009 | 160 |
| | | .0004 | 142 |

TABLE 2

| Compound | Schedule of Treatment (ip) | Dose mole/Kg. | T/C % |
|---|---|---|---|
| 14-Methoxydaunomycin | On days 5, 9, 13 | .0210 | 123 |
| Daunomycin-HCl | On days 5, 9, 13 | .0142 | 126 |

In Table 1, two compounds according to the invention have been compared to daunomycin in a test in which mice infected with tumor cells are treated with 9 daily injections starting from the first day of transplantation. The novel 14-alkoxy derivatives show an antitumor activity comparable to that of daunomycin. Moreover, 14-phenoxyJaunomycin is clearly better tolerated since it displays its activity in a larger range of doses, thus showing a reduced toxicity as compared to daunomycin.

In Table 2 a different schedule, better suited for the evaluation of daunomycin analogues, was used. The injections are made on days 5, 9 and 13 with a 4 day internal between each single injection starting from the fifth day after tumor transplantation in mice. In this test, 14-methoxydaunomycin shows virtually the same activity as daunomycin itself.

Variations and modifications can, of course, be made without departing from the spirit and scope of the invention.

Having thus described our invention, what we desire to secure by Letters Patent and hereby claim is:

1. A compound of the formula:

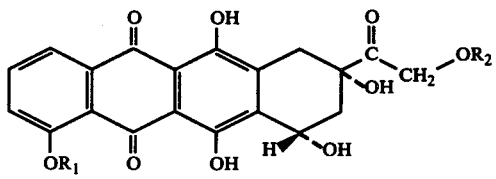

wherein $R_1$ is hydrogen or a lower alkyl having from 1 to 4 carbon atoms and $R_2$ is a lower alkyl having from 1 to 4 carbon atoms, cycloalkyl having from 3 to 6 carbon atoms, phenyl, lower alkyl phenyl, lower alkoxy phenyl or halophenyl.

2. A compound according to claim 1, which is 14-methoxydaunomycinone.

3. A compound according to claim 1, which is 14-ethoxydaunomycinone.

4. A compound according to claim 1, which is 14-isopropyloxydaunomycinone.

5. A compound according to claim 1, which is 14-phenoxydaunomycinone.

6. A compound according to claim 1, which is o-methylphenoxydaunomycinone.

7. A compound according to claim 1, which is p-methoxyphenoxydaunomycinone.

8. A compound according to claim 1, which is m-methoxyphenoxydaunomycinone.

9. A compound according to claim 1, which is p-chlorophenoxydaunomycinone.

10. A process for preparing a compound as claimed in claim 1, said process comprising reacting a 14-bromodaunomycinone of the formula:

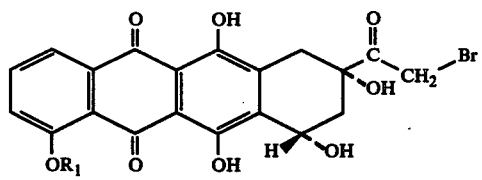

wherein $R_1$ is as defined in claim 1 with tosylhydrazine to form a 13-tosylhydrazone, dissolving said 13-tosylhydrazone at a temperature between 0° and 50° C. in an alcohol of the formula $R_2OH$, wherein $R_2$ is as defined in claim 1, treating the thus obtained solution with silver trifluoromethansulphonate or an alkali metal carbonate or hydroxide, to obtain a compound of the formula:

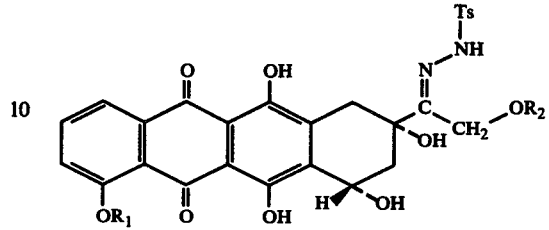

wherein $R_1$ and $R_2$ are as defined above and Ts is tosyl, and refluxing said compound (V) in acetone, in the presence of p-toluensulphonic acid, to form the compound of claim 1.

11. A process according to claim 10, wherein the alkali metal carbonate or hydroxide is sodium carbonate, sodium hydroxide, potassium carbonate or potassium hydroxide.

12. A compound of the formula:

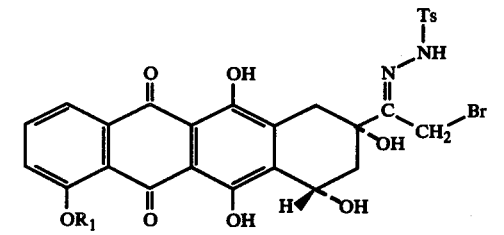

or

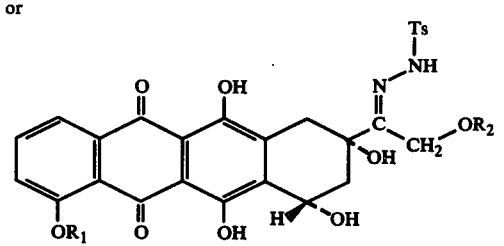

wherein Ts is tosyl, $R_1$ is hydrogen or a lower alkyl having from 1 to 4 carbon atoms and $R_2$ is a lower alkyl having from 1 to 4 carbon atoms, cycloalkyl having from 3 to 6 carbon atoms, phenyl, lower alkyl phenyl, lower alkoxy phenyl or halophenyl.

* * * * *

UNITED STATES PATENT AND TRADEMARK OFFICE
CERTIFICATE OF CORRECTION

PATENT NO. : 4,134,903
DATED : January 16, 1979
INVENTOR(S) : Paolo Masi, et al.

It is certified that error appears in the above—identified patent and that said Letters Patent is hereby corrected as shown below:

Second line of Abstract, Formula II:" 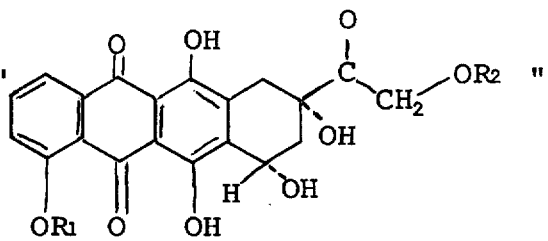 "

should read -- 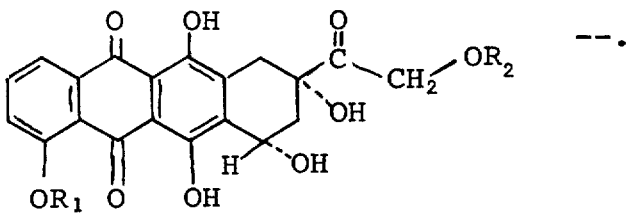 --.

Col. 1, Line 25: "amamalian" should read -- mammalian --.

Col. 8, line 58: "14-phenoxyJaunomycin" should read
-- 14-phenoxydaunomycin --.

Signed and Sealed this

Sixth Day of October 1981

[SEAL]

Attest:

GERALD J. MOSSINGHOFF

Attesting Officer     Commissioner of Patents and Trademarks